United States Patent [19]

Polaschegg et al.

[11] Patent Number: 5,049,047
[45] Date of Patent: Sep. 17, 1991

[54] INFUSION PUMP WITH MEANS FOR MEASURING THE TUBE INTERNAL DIAMETER

[76] Inventors: Hans-Dietrich Polaschegg, Grünwiesenweg 9, 6370 Oberursel 4; Robert Kroh, Pfaffenwiesbacherstr. 27a, 6393 Wehrheim 1; Gerd Krick, Kaiser-Friedrich-Promenade 92, 6380 Bad Homburg v.d.H., all of Fed. Rep. of Germany

[21] Appl. No.: 451,278

[22] Filed: Dec. 15, 1989

[30] Foreign Application Priority Data

Dec. 16, 1988 [DE] Fed. Rep. of Germany ....... 3842404

[51] Int. Cl.$^5$ .............................................. F04B 43/12
[52] U.S. Cl. ...................................... 417/474; 417/18; 73/198; 604/67
[58] Field of Search .......... 417/1, 18, 45, 63, 474-477; 604/67; 73/198

[56] References Cited

U.S. PATENT DOCUMENTS

| | | |
|---|---|---|
| Re. 30,088 | 9/1979 | Lund et al. |
| 3,850,026 | 11/1974 | Lund et al. |
| 4,108,575 | 8/1978 | Schäl .............................. 417/477 X |
| 4,526,515 | 7/1985 | De Vries ............................ 417/63 |
| 4,545,744 | 10/1985 | Weber et al. |
| 4,702,675 | 10/1987 | Aldrovandi et al. ........... 417/477 X |
| 4,976,590 | 12/1990 | Baldwin ................................ 417/53 |

FOREIGN PATENT DOCUMENTS

| | | |
|---|---|---|
| 263796 | 2/1912 | Fed. Rep. of Germany. |
| 1710902 | 8/1955 | Fed. Rep. of Germany. |
| 1491770 | 4/1970 | Fed. Rep. of Germany. |
| 2148976 | 4/1972 | Fed. Rep. of Germany. |
| 2555291 | 6/1977 | Fed. Rep. of Germany. |
| 3326784 | 2/1985 | Fed. Rep. of Germany. |
| 646517 | 11/1984 | Switzerland. |

OTHER PUBLICATIONS

Krautkraemer et al., Werkstoffpruefung mit Ultraschall, pp. 562-565 (Jun. 1986).

Primary Examiner—Leonard E. Smith
Assistant Examiner—Eugene L. Szczecina, Jr.
Attorney, Agent, or Firm—Nilsson, Robbins, Dalgarn, Berliner, Carson & Wurst

[57] ABSTRACT

An infusion pump system comprising means for measuring internal diameter of an associated pump supply tube formed from a flexible material, such as plastic or rubber. The means for measuring internal diameter may comprise an ultrasound system including at least one transmiter and one receiver, as well as an evaluation unit. Alternatively, a mechanical system may be employed in the form of a counterpressure unit arranged perpendicular to the axis of the supply tube and including a movable plunger and an abutment surface for compression of the supply tube to be measured. A measurement and evaluation unit associated with the counterpressure unit determines the distance traversed by the movable plunger. The internal diameter of the tube may be determined by generating a force-displacement diagram. In accordance with one embodiment, the movable plunger is a pumping rod of a linear peristaltic pump.

7 Claims, 8 Drawing Sheets

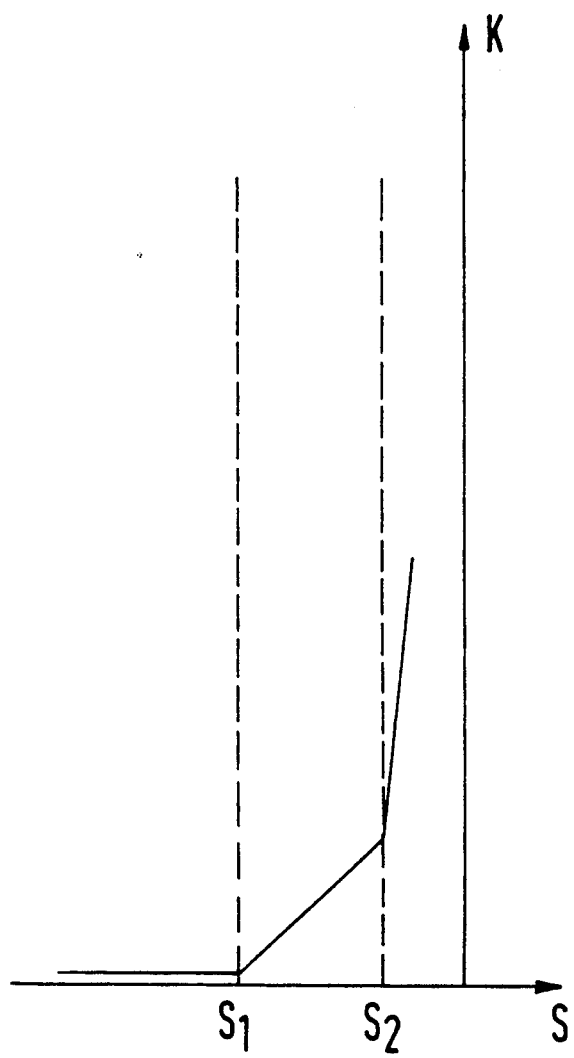

INFUSION PUMP WITH MEANS FOR MEASURING THE TUBE INTERNAL DIAMETER

The invention relates to an infusion pump with a conveyer or supply tube comprising a flexible material such as plastic or rubber.

Modern intensive care of seriously ill patients makes necessary the precise administration of medications as well as the parenteral administration of appropriate nourishment. In a few critical cases, for example the administration of pure liquid after operations, a so-called gravity infusion system may be used. In such a system, the rate of infusion is established through manual changes in the flow resistance of an infusion conduit with the aid of e.g. a roller clamp. The infusion rate is evaluated by determining the drop rate in a drop chamber of the infusion apparatus.

A somewhat greater accuracy is achieved with a so-called infusion regulator. In such a system, gravity is similarly used for advancing the liquid, but flow resistance is regulated through a suitable automatic device in a manner such that a predetermined drop rate is maintained.

In those instances where gravity is not sufficient to overcome the flow resistance of the attached conduits, for example on account of associated filters or catheters, it is necessary to employ so-called infusion pumps. In this regard, one may make a distinction in substance among drop regulated pumps, volumetric pumps and spray pumps.

Drop regulated pumps have the fundamental disadvantage, that a precise administration (in the sense of predetermining the amount of an active agent administered) is not possible, as the drop volume is subject to variations of up to 400% in dependence on the physical properties of the medium for administration. This drop volume is primarily affected by the surface tension of the medium, which may be modified when a medication is added to a carrier solution.

Volumetric pumps and spray pumps operate as a rule using electronically regulated advancing mechanisms, whose aberrations from rated value are below about 5%. The accuracy of these pumps is at least to some extent determined by the accuracy of the associated disposable components. With respect to spray pumps the relevant feature is the internal diameter of the sprayer or injector; with peristaltic pumps, the feature is the internal diameter of the conveyer tube.

On account of the high accuracy of the sprayers or injectors for use with spray pumps, effective accuracies on the order of about 2% are achieved. On the other hand, the accuracy with peristaltic pumps is in the magnitude of 5 to 10% even with the use of qualitatively high quality tubes, on account of the allowable variation in the internal diameter thereof.

While spray pumps customarily operate in the range of administration rates of from <1 to 100 ml/h with a resolution of about 0.1 ml/h, peristaltic infusion pumps in the best case permit an administration range from 1 ml/h to a maximum of 1,000 ml/h with a resolution of about 1 ml/h. From this it should be noted, that with low rates (typically <10 ml/h) the fluctuations in administration rate over short observation periods are exceptionally high, and thus such pumps are not suitable for administration of medications having short half-life periods (e.g., blood pressure regulators or anesthetics) at low rates of administration.

These rate deviations are conditioned by the periodicity of the peristaltics. This effect is heightened as the administration volume of a pumping cycle (i.e., a revolution of the pump head in a rotary peristaltic pump or a complete sequence with a linear peristaltic pump) increases, or in other words, dependent on the internal diameter of the pump tube.

If one decreases the tube internal diameter for example by a factor of 3.15, then the cross-sectional area of the pump tube and thus the administration rate is decreased by a factor of 10 for the same pump rate. Thus if one operates a peristaltic pump with such a tube of decreased internal diameter, the variations in administration rate are reduced by a factor of 10 at low rates and fixed observation intervals.

Peristaltic pumps for medical purposes are known which permit the use of various disposable components and employ systems which enable an automatic determination of the characteristics of the disposable components.

For example, German Patent 33 26 784 discloses a mechanical coding of the disposable components. This coding presupposes, however, that both the pump and the disposable components must have available the corresponding special systems. This has the disadvantage, that an additional expenditure is necessary, while the desired and necessary security is nonetheless not achieved, as mistakes may occur also in the preparation of the disposable components, as is indicated for example by the Medical Device Reporting Register of the Food and Drug Administration.

German Gebrauchsmuster DE-GM 17 10 902 discloses a measuring device for the continuous measurement of the diameter of tubes. The tube to be measured is advanced through a slot or gap formed by two rollers and compressed together. The width of the compressed tube is determined by means of two coils or wheels, which have the form of Archimedes spirals. On account of the predetermined, fixed width of the gap the measurement result is not accurate. In any event, a determination of the internal diameter of the tube is not possible.

German Patent DE-PS 263 796 discloses an apparatus for determination of the breadth of bodies in the form of tubes, whereby the tube is stretched using two bars or shafts introduced into the tubes. With such an apparatus, only relatively thin-walled tubes with large diameters can be measured. Moreover, the apparatus is mechanically burdensome and subject to substantial errors.

German Ausleoeschrift DE-AS 21 48 976 describes apparatus for determination of the cross-sectional area of metal pipes, whereby an ultrasound apparatus is employed. The internal diameter is calculated from the internal diameter as well as the determined thickness of the wall. The metal pipe is measured for control purposes after manufacture and before filling or mounting in an installation.

The object of the present invention is to provide an infusion pump with improved accuracy of administration and safety.

SUMMARY OF THE INVENTION

In accordance with the present invention, there is provided an infusion pump system comprising means for measuring internal diameter of an associated pump supply tube formed from a flexible material, such as plastic or rubber. The means for measuring internal diameter may comprise an ultrasound system including at least one transmitter and one receiver, as well as an evaluation unit. Alternatively, a mechanical system may be employed in the form of a counterpressure unit arranged perpendicular to the axis of the supply tube and including a movable plunger and an abutment surface for compression of the supply tube to be measured. A measurement and evaluation unit associated with the counterpressure unit determines the distance traversed by the movable plunger. The internal diameter of the tube may be determined by generating a force-displacement diagram.

BRIEF DESCRIPTION OF THE DRAWINGS

FIG. 5 is a force-distance diagram as is generated during compression of a tube;

DETAILED DESCRIPTION OF THE INVENTION

Figure 1:
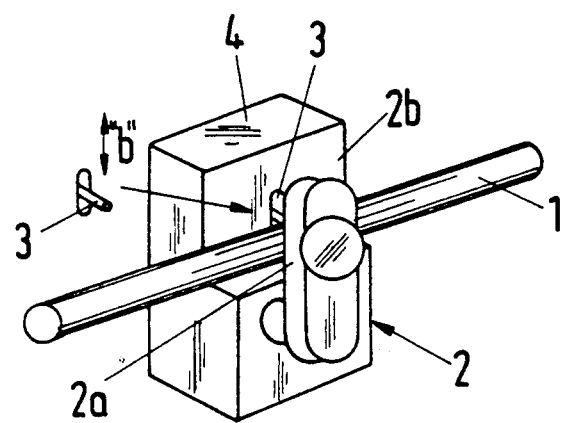
FIG. 1 is a perspective illustration of a system for measurement of the internal diameter according to one embodiment.

The apparatus for measurement of the internal diameter of a tube may be arranged before, after or in the pumping area of the infusion pump. It is thereby possible to determine automatically the internal diameter of the administration line, register the results and compare or adjust them with a set-up arrangement, for example prior to placing the infusion pump in operation. When a roller pump is equipped with an apparatus for measuring the internal diameter, the stream volume can be very accurately determined and a high administration accuracy can be achieved through a corresponding calculation in the associated evaluation unit of the internal diameter based on the cross-section with inclusion of the rotation rate of the roller pump.

According to a first embodiment the apparatus is provided with at least one counterpressure device, which is arranged perpendicular with the axis of the tube and which comprises in essential elements a movable plunger and an abutment surface. This movable plunger serves to compress the tube to be measured, until the inner walls of the tube lie one on top of the other. This counterpressure device is attached to a measurement and evaluation unit, which is provided for determination of the distance traversed by the plunger. Upon consideration of the thickness of the wall of the tube, the internal diameter of the tube can be ascertained on the basis of the distance traversed by the plunger.

As the wall thickness of the tube is subject to not inconsiderable permissible variation, a higher accuracy may be achieved according to a further embodiment of the invention, where the measurement and evaluation unit is arranged for determination of a force-displacement diagram. In this arrangement, the force of the plunger in compression of the tube is measured. From the time the plunger contacts the external wall of the tube to be measured, the necessary force increases linearly, until the internal walls of the tube lie one on top of the other. From this point, the slope of the force-displacement straight line increases once again. From the distance segment determined by the beginning and the end of the linear increase in force, the internal diameter of the tube may be ascertained.

According to a particular embodiment of the invention the plunger is the pumping rod of a linear peristaltic pump. This has the advantage, that no additional measurement device must be attached to the tube. Rather, only one pumping rod of the peristaltic must be arranged for force-displacement measurement, whereby the necessary evaluation may be effected by an evaluation unit integrated in the peristaltic pump. This arrangement offers the further advantage, that with every pump cycle the internal diameter of the pump line can be monitored, so that in combination with the cycle frequency a continuous surveillance of the stream volume is possible. In this manner, a very high accuracy of administration is achieved with the use of standard infusion equipment.

In place of a force-displacement measurement, in accordance with a further embodiment of the invention a double-displacement measurement may be made. In this case, an additional measurement baffle is contemplated, which is perpendicular to the axis of the tube and perpendicular to the direction of movement of the plunger. Through the assistance of this measurement baffle, which in all cases is connected with the measurement and evaluation unit, the maximum diameter of the tube as compressed by the plunger is determined. From the two measurements a and b, which represent respectively the minimum external diameter of the tube after compression and the maximum external diameter of the deformed tube as measured by the measurement baffle, the internal diameter of the tube may be calculated using the following formula:

$$d = (b-a) \times 2/\pi.$$

The determination of the quantities a and b, as well as the calculation therefrom, may be effected in a variety of techniques: mechanically, optically, hydraulically, electrically or through some combination thereof.

According to a preferred embodiment, the plunger and measurement baffle are combined with a piston of a hydraulic system, so that through the appropriate selection of the piston surface and the amount of liquid displaced by the piston, the internal diameter may be indicated directly by means of a corresponding indicator device. According to a further embodiment, the plunger and measurement baffle are associated with a measurement bridge, which comprises in substance two potentiometers.

Instead of determining the internal diameter of the tube in a mechanical manner, according to another embodiment an ultrasound apparatus is used, comprising at least one ultrasound transmitter adjacent to the outside of the pump tube and at least one ultrasound detector also adjacent to the outside of the pump tube, both of which are connected to a measurement and evaluation unit, and arranged for determination of the internal diameter through a flowtime measurement.

The arrangement of ultrasound transmitter and ultrasound received can be carried out in various manners. Thus, the transmitter and receiver can lie facing one another, or else the transmitter and receiver can be arranged in such a manner, that a flow-time measurement may be carried out under an angle of reflection of >0°. Advantageously, the reflection flow-time measurement is carried out under an angle of reflection of 45°.

The ultrasound transmitter and ultrasound receiver can also be combined into a single sensor, whereby in this case the angle of reflection amounts to 180°.

As peristaltic infusion pumps are in a position to generate a reduced pressure or vacuum on the suction side, they must therefore have at their disposal an air detector downstream to detect air or air bubbles in the tube. As air detectors customarily operate on ultrasonic principles, according to a further preferred embodiment the ultrasonic apparatus for determination of the internal diameter of a tube may include such an ultrasound air detector, whereby the evaluation unit is arranged additionally for determination of the internal diameter of the tube by flow-time measurements.

With the aid of the inventive apparatus, the determination of tube internal diameter is possible directly before, after or in the pumping area of an infusion pump, whereby for example with a peristaltic pump the internal diameter of the pump tube and thereby the feed capacity of the peristaltic pump can be permanently controlled without a large additional technical expenditure, so that variations in the internal diameter of the tube on account of fatigue of the tube material during the pumping operation can also be noted.

Figure 9A:
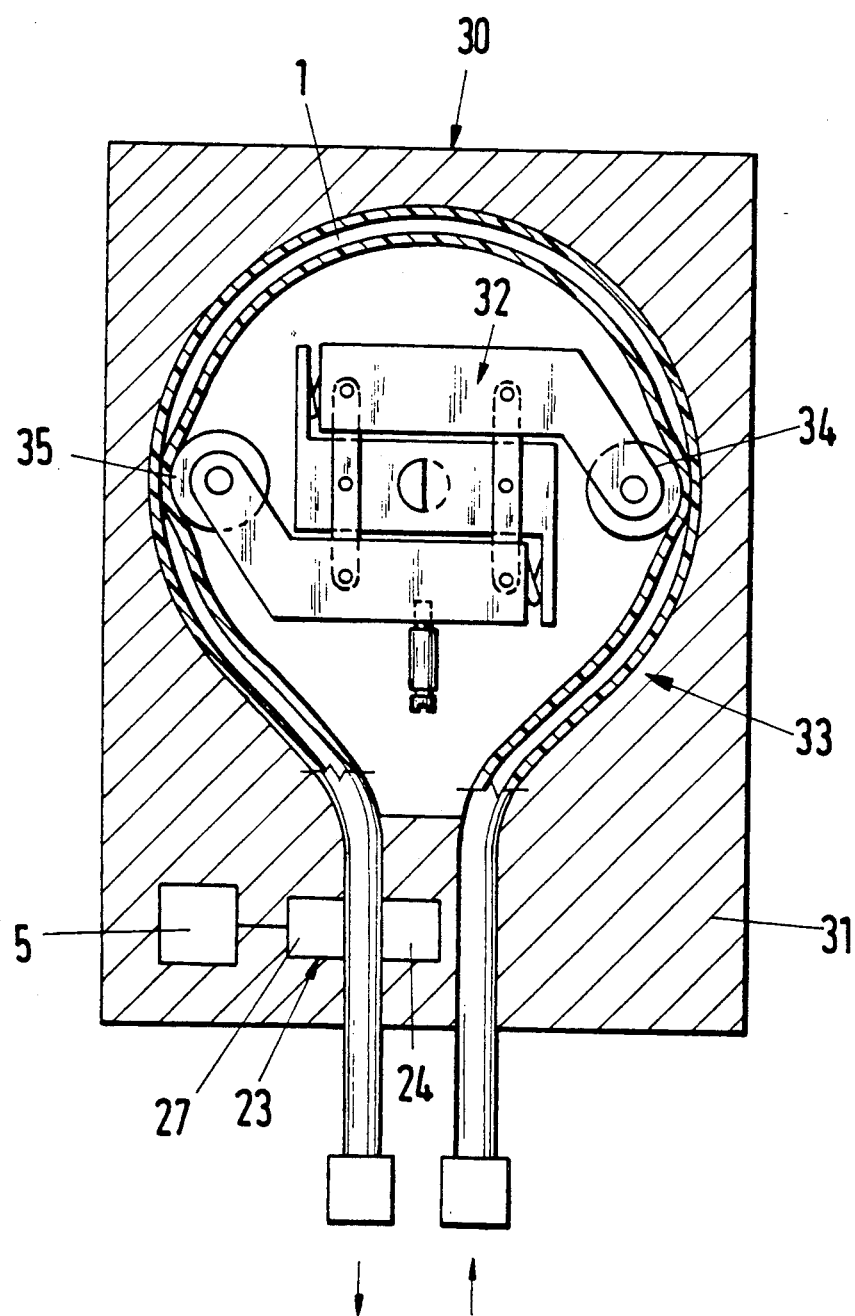
FIG. 9a is a roller pump with an ultrasound system.

FIG. 9a illustrates a peristaltic roller pump 30, comprising a stator portion 31 and a rotor 32. In the stator portion 31 a pump bed 33 is formed for receipt of the pump tube 1. In the rotor 32 rollers 34, 35 which press against the pump tube 1 are positioned for rotary motion.

Figure 7:
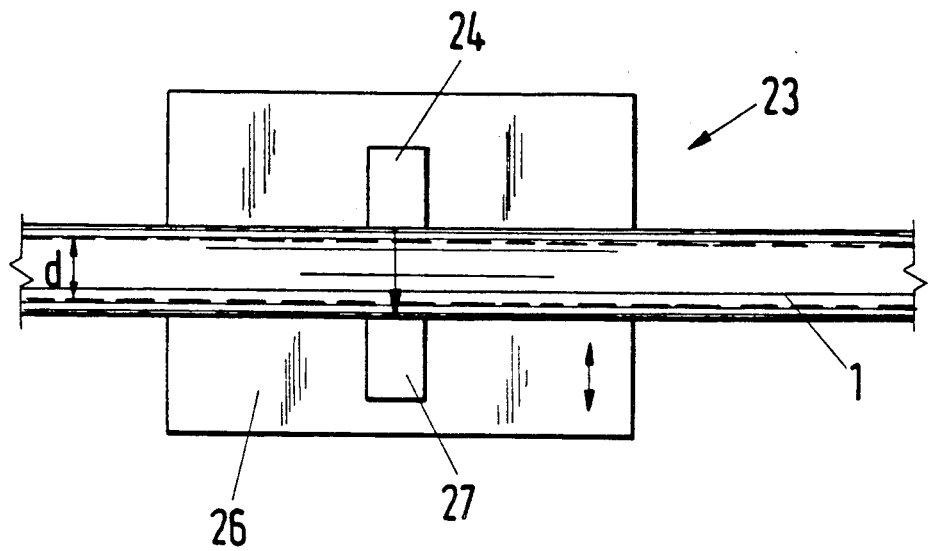
FIG. 7 is an ultrasound system according to a first embodiment.
Figure 8:
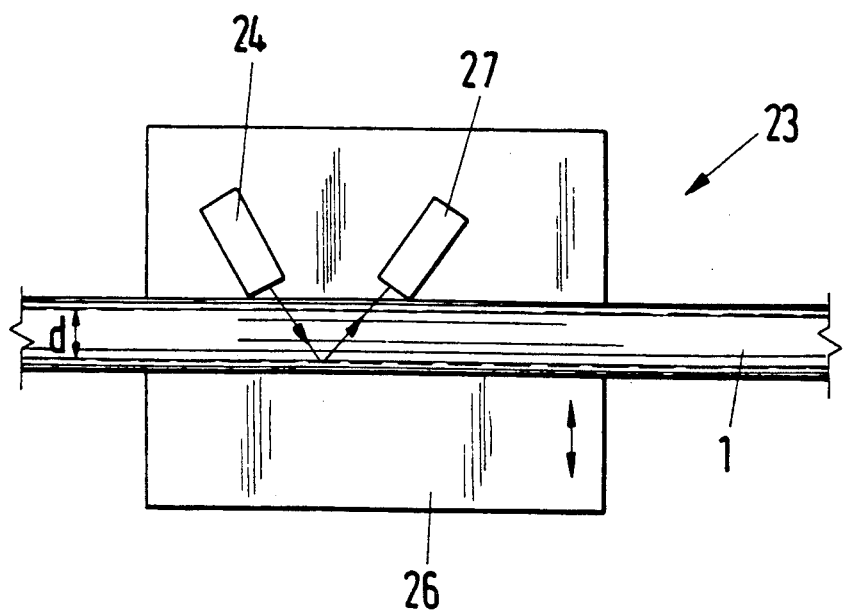
FIG. 8 is an ultrasound system according to a further embodiment.

In the lower portion of the stator 31 in the area of the outlet end of the tube 1, an ultrasound system 23 is arranged for measurement of the internal diameter of the tube 1. The ultrasound system 23 comprises a transmitter 24, a receiver 27 and also a measurement and evaluation system 5. Two possible embodiments of the ultrasound system are illustrated in FIGS. 7 and 8, respectively.

Figure 6A:
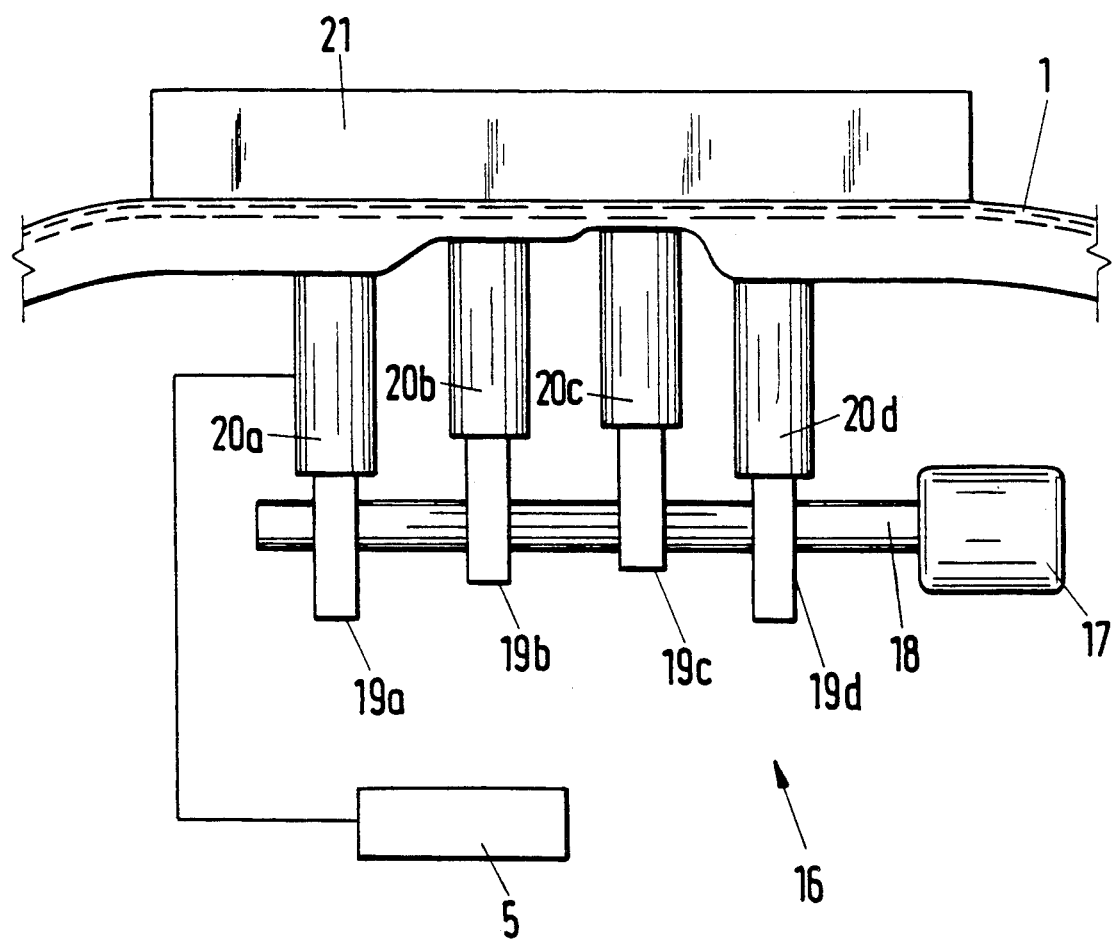
FIG. 6a and b are each schematic depictions of a linear peristaltic pump according to two further embodiments.
Figure 6B:
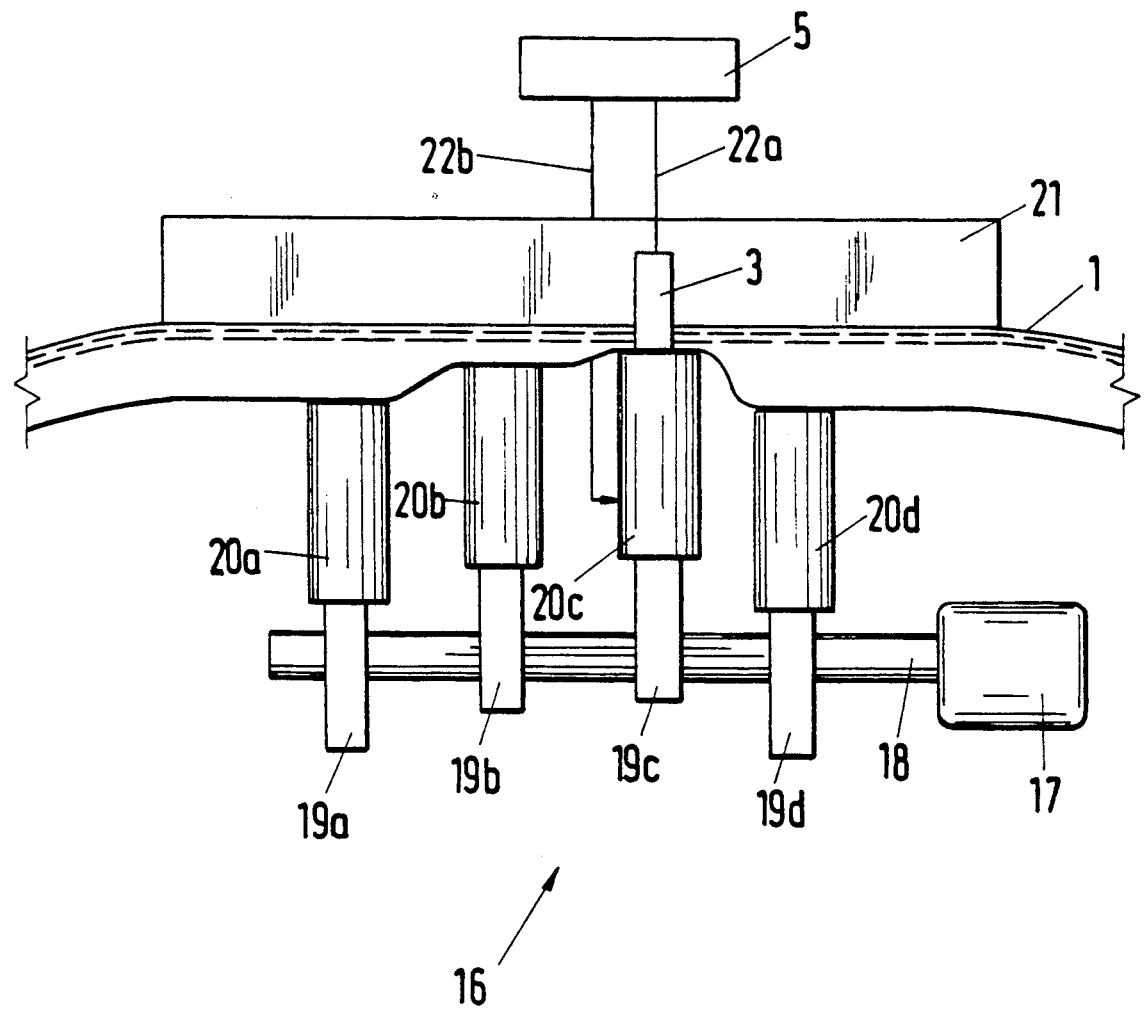
Figure 9B:
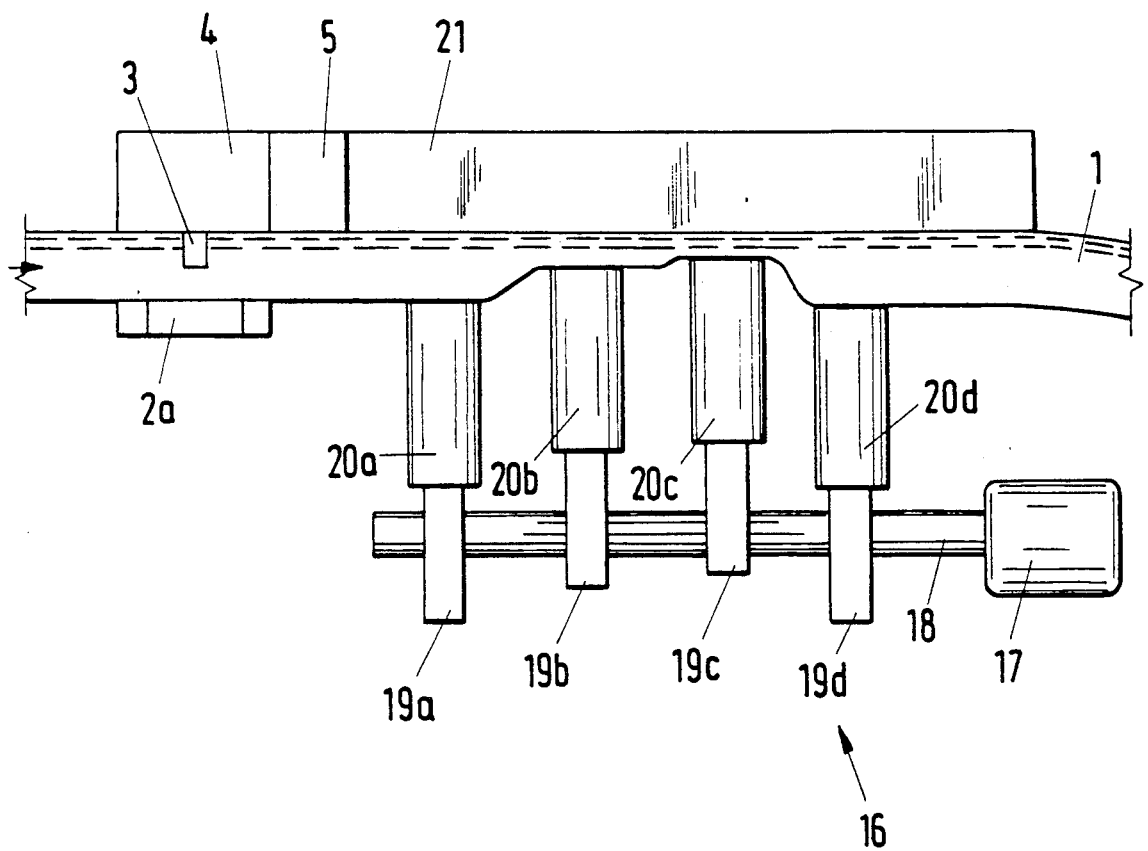
FIG. 9b is a linear peristaltic pump with a superimposed mechanical system for measurement of the internal diameter.

In FIG. 9b a linear peristaltic pump is schematically illustrated, which pump is described in greater detail in conjunction with FIG. 6a and 6b. At the pump inlet a mechanical system for measurement of the internal diameter of the tube 1 is arranged, comprising an angular housing 4 and a movable plunger 2a, a measurement baffle 3 as well as an evaluation system 5.

Figure 2:
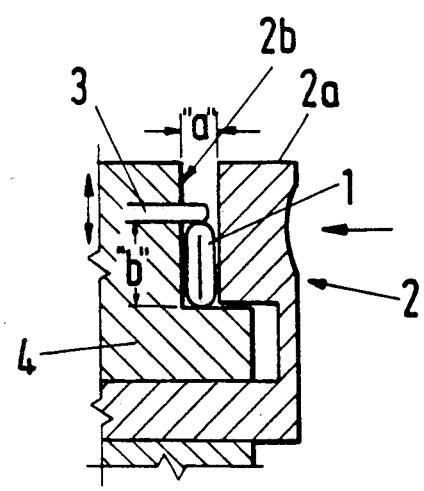
FIG. 2 is a cross-section through the apparatus according to FIG. 1.

FIG. 1 provides a perspective illustration of a system for measurement of the internal diameter of a tube 1. The angular housing 4 is provided with internal angular surfaces serving for receipt of the tube 1 to be measured. The perpendicular angular surface 2b serves as abutment surface and is arranged parallel to the planar surface of the plunger 2a of the counterpressure device 2. This plunger 2a is movably arranged in the housing and is combined with an actuator or drive, so that the plunger can be moved in the direction towards the abutment surface 2b, whereby the tube 1 is deformed in the manner which is to be seen in FIG. 2. The measurement baffle 3, which during the deformation of the tube 1 by the plunger 2a is deflected upwards, is arranged in the abutment surface 2b. When the tube 1 is completely deformed, the interval a between the surface of the plunger and the abutment surface 2b is determined from the distance covered by the course of the plunger 2a. Simultaneously, the deflection b of the measurement baffle 3 is measured and in the measurement and evaluation unit accommodated in the housing 4 the internal diameter of the tube 1 is determined according to the formula $(b-a) \times 2/\pi$.

Figure 3:
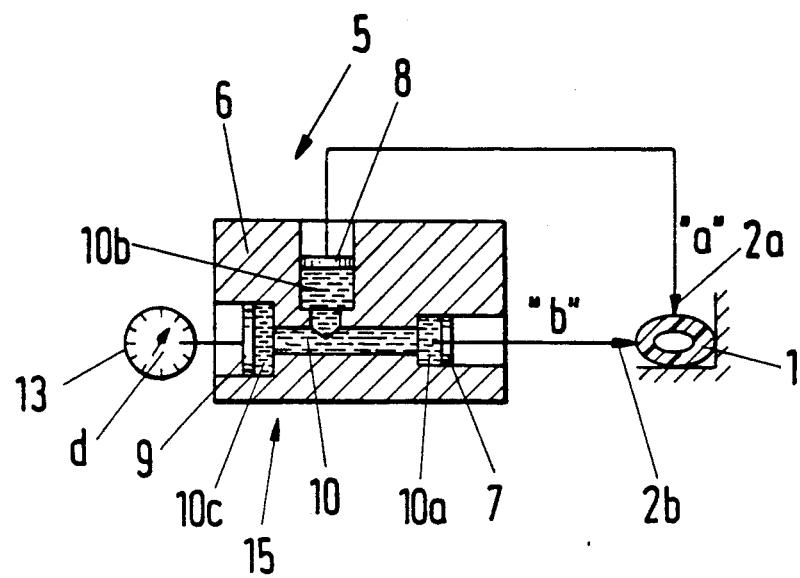
FIG. 3 is a schematic depiction of a hydraulic measurement system.

FIG. 3 is a schematic illustration of a hydraulic measurement system. The tube 1 is also in this case deformed by the plunger 2a, whereby the maximum external diameter is measured by the measurement baffle 2b after deformation. Plunger 2a and measurement baffle 2b are represented in FIG. 3 by corresponding arrows. The plunger 2a and the measurement baffle 2b are each combined with a piston 8 and 7, respectively, of a hydraulic system. These pistons 7 and 8 are arranged in correspondingly dimensioned terminal passages 10a and 10b, respectively, of a common canal 10, which is combined over a third canal passage 10c with a further piston 9, which is connected to an indicator device 13. Through appropriate selection of the piston surfaces the factor $2/\pi$ is taken into account by the indicator.

Figure 4:
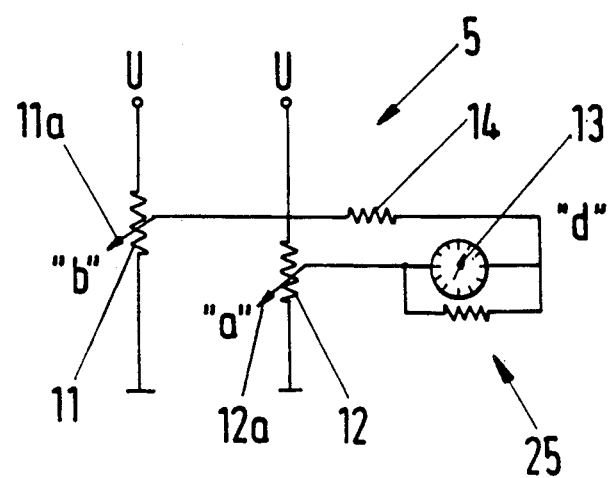
FIG. 4 is a schematic depiction of an electrical measurement system.

FIG. 4 depicts a measurement and evaluation unit 5, comprising a measurement bridge 25. The plunger 2a and the measurement baffle 3 are each connected to a potentiometer 12 and 11, respectively. Based on the differential positioning of the corresponding receivers 11a and 12a of potentiometers 11 and 12 through the position of the measurement baffle 3 and the plunger 2a, a potential difference is registered at the receivers, which may be read as the internal diameter d from the indicator device 13. Through suitable dimensioning of the resistors 11, 12 and 14 the factor $2/\pi$ is taken into account.

If the plunger 2a is provided with a force-displacement receiver and the evaluation unit arranged for plotting a force-displacement diagram, the measurement baffle 3 can be eliminated. In FIG. 5 such a force-displacement diagram is illustrated. As long as the plunger is still not in contact with the external wall of the tube 1, the expended force is near zero. As soon as the plunger contacts the external wall of the tube 1, which is at point S1 in FIG. 5, the expended force increases linearly until point S2 is reached, where the internal walls of the tube 1 lie one on top of the other. The subsequent force-displacement curve is determined by the elastic properties of the tube walls. Now a higher expenditure of force corresponding thereto is also necessary, which is reflected in a greater slope in the force-displacement curve. The segment of the curve between S1 and S2 then provides directly the internal diameter of the measured tube 1.

In FIGS. 6a and 6b two further embodiments are illustrated, which come into use with a linear peristaltic pump 16. FIG. 6a schematically illustrates such a linear peristaltic pump. Over a combined drive shaft 18, which is associated with a drive motor 17, the pump impacting rods 20a through 20d are pressed against the tube 1 through the cam plates 19a through 19d in such a manner, that the tube is deformed in the manner of a peristaltic movement. The plate 21 serves as an abutment surface, on which the tube 1 lies. In the embodiment illustrated herein, the pump impacting rod 20a is provided with a force-displacement register, which is connected to an appropriate measurement and evaluation unit 5. Through evaluation of the force-time diagram, as illustrated in FIG. 5, the internal diameter is determined. The advantage of this arrangement lies in that with every pump cycle the internal diameter of the tube may be measured, so that a permanent monitoring of the flow rate of the peristaltic pump 16 is possible.

In FIG. 6b the same peristaltic pump is illustrated, but here the pump impacting rod 20c is not provided with a force-displacement register. The manner of operation of the system illustrated here corresponds to that of the arrangement depicted in FIG. 1. The pump impacting rod 20c effects the deformation of the tube 1. The abutment plate 21 is provided in the vicinity of pump impacting rod 20c with a measurement baffle 3, which is deflected during the deformation of the tube 1, as already described with respect to FIGS. 1 and 2. The pump impacting rod 20c is connected to the evaluation unit 5 via electrical lead 22b and the measurement baffle 3 is likewise connected to the evaluation unit 5 via electrical lead 22a.

FIG. 7 illustrates an ultrasound system 23, which comprises a transmitter 24 and a receiver 27 in addition to a measurement and evaluation unit not here illustrated. In the exemplary embodiment of FIG. 7 the transmitter is arranged opposite the receiver. The receiver is found on a movable plate 26, which can be displaced after insertion of the tube 1, so that the receiver lies against the external wall of the tube 1 to be measured. From the propagation time of the ultrasound signal between the transmitter 24 and the receiver 27 the internal diameter d of the tube 1 is determined in the measurement and evaluation unit 5, where the thickness of the walls of the tube 1 must be taken into account.

In FIG. 8 the ultrasound transmitter 24 and the ultrasound receiver 27 are arranged in a reflection position. In the exemplary embodiment here illustrated, the ultrasound wave is reflected on the internal wall of the tube 1 over an angle of about 45°.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. An infusion pump system comprising:
   a supply tube formed from a flexible material;
   pump means for advancing a liquid through said supply tube; and
   means for measuring internal diameter of said supply tube comprising a counterpressure device arranged perpendicular to an axis of said supply tube, said counterpressure device including a movable plunger and a corresponding abutment surface for complete compression of said supply tube, and an associated measurement and evaluation unit for calculating the internal diameter of said supply tube based on distance traversed by said movable plunger.

2. An infusion pump system according to claim 1, wherein the movable plunger has a planar surface and said abutment surface is parallel thereto.

3. An infusion pump system according to claim 1, wherein said measurement and evaluation unit is arranged for generating a force-displacement diagram of the counterpressure device and for determining the internal diameter of said supply tube from said force-displacement diagram.

4. An infusion pump system according to claim 1, further comprising at least one measurement baffle perpendicular to said axis of said supply tube and to a direction of movement of said counterpressure device for measurement of maximum external diameter of said supply tube after said compression.

5. An infusion pump system according to claim 1, wherein said movable plunger comprises a pumping rod of a linear peristaltic pump.

6. An infusion pump system according to claim 1, wherein said measurement and evaluation unit comprises a hydraulic measurement system.

7. An infusion pump system according to claim 1, wherein said measurement and evaluation unit comprises a resistance measurement bridge.

* * * * *